United States Patent [19]

Maeda et al.

[11] Patent Number: 5,302,979
[45] Date of Patent: Apr. 12, 1994

[54] OPHTHALMIC APPARATUS CAPABLE OF MEASURING THE SHAPE OF A CORNEA

[75] Inventors: Yasuo Maeda, Kawasaki; Takashi Masuda, Yamato, both of Japan

[73] Assignee: Canon Kabushiki Kaisha, Tokyo, Japan

[21] Appl. No.: 945,583

[22] Filed: Sep. 16, 1992

Related U.S. Application Data

[63] Continuation of Ser. No. 557,773, Jul. 26, 1990, abandoned.

[30] Foreign Application Priority Data

Jul. 28, 1989 [JP] Japan .................. 1-195631
Sep. 11, 1989 [JP] Japan .................. 1-236311

[51] Int. Cl.$^5$ .............................. A61B 3/10
[52] U.S. Cl. ...................... 351/212; 351/211; 351/247
[58] Field of Search .......... 351/211, 212, 247, 205, 351/208

[56] References Cited

U.S. PATENT DOCUMENTS

| | | |
|---|---|---|
| 4,660,946 | 4/1987 | Nakamura et al. |
| 4,666,269 | 5/1987 | Nakamura et al. |
| 4,704,012 | 11/1987 | Kohayakawa et al. |
| 4,710,003 | 12/1987 | Masuda et al. |
| 4,764,006 | 8/1988 | Hamano et al. |
| 4,796,989 | 1/1989 | Fukuma et al. ............ 351/212 |
| 4,859,051 | 8/1989 | Fukuma et al. ............ 351/212 X |

FOREIGN PATENT DOCUMENTS

59-118131 7/1984 Japan .
61-249432 11/1986 Japan .

Primary Examiner—Scott J. Sugarman
Assistant Examiner—Hung Xuan Dang
Attorney, Agent, or Firm—Fitzpatrick, Cella, Harper & Scinto

[57] ABSTRACT

An ophthalmic apparatus includes a first index mark provided as an index mark for measuring the shape of a cornea substantially on the optic axis, a second index mark provided around the optic axis, and a calculator for calculating the shape of the cornea based on the position information of the cornea-reflected image of the first and second index marks.

40 Claims, 5 Drawing Sheets

OPHTHALMIC APPARATUS CAPABLE OF MEASURING THE SHAPE OF A CORNEA

This application is a continuation of application Ser. No. 07/557,773, filed Jul. 26, 1990, which is now abandoned.

BACKGROUND OF THE INVENTION

1. Field of the Invention

This invention relates to an ophthalmic apparatus capable of measuring the shape of the cornea of an eye to be examined.

2. Related Background Art

In an apparatus for measuring the shape of the cornea of an eye to be examined, as disclosed in U.S. Pat. No. 4,660,946, a ring-shape index mark or a plurality of calescence point index marks disposed on the circumference of the same circle are projected onto the cornea of an eye to be examined, and from the shapes and positions of the reflected images thereof, an ellipse passing through those reflected images is specified, whereby the shape of the cornea is calculated and measured.

In the above-described example of the prior art, however, even in the case of a cornea of so-called bad astigmatism the shape differs from the normal shape of which calculation and measurement is effected so that an ellipse may be forcibly formed, and this has led to the problem that in spite of being a cornea of bad astigmatism, such a cornea is mistaken for a cornea of normal shape. This is attributable to the fact that in the above-described example of the prior art, the center of the ellipse is indirectly found by calculation, and this means that there is the above-noted problem with regard to bad astigmatism.

It is proposed in Japanese Laid-Open Patent Application No. 59-118131 by the assignee of the present invention to provide a plurality of concentric ring-shape index marks so that the measurement of the shape of a cornea may be possible, even if the cornea has bad astigmatism, indirectly to find the center of an ellipse by calculation on the basis of one of the ring-shaped index mark images, and to find the shape of the cornea by the center of the ellipse and the other ring-shaped index mark images. However, this also fins indirectly the center of the ellipse by calculation as described above and therefore suffers from the problem that if the cornea has bad astigmatism, the original center of the ellipse cannot be specified.

SUMMARY OF THE INVENTION

It is an object of the present invention to provide an ophthalmic apparatus which can directly specify the center of the ellipse of the cornea-reflected image of an index mark for finding the shape of the cornea of an eye to be examined.

It is a further object of the present invention to provide an ophthalmic apparatus in which an index mark for measuring the eye refractive power information of an eye to be examined is used also as an index mark for measuring the shape of the cornea of the eye to be examined.

DESCRIPTION OF THE PREFERRED EMBODIMENTS

Figure 1:
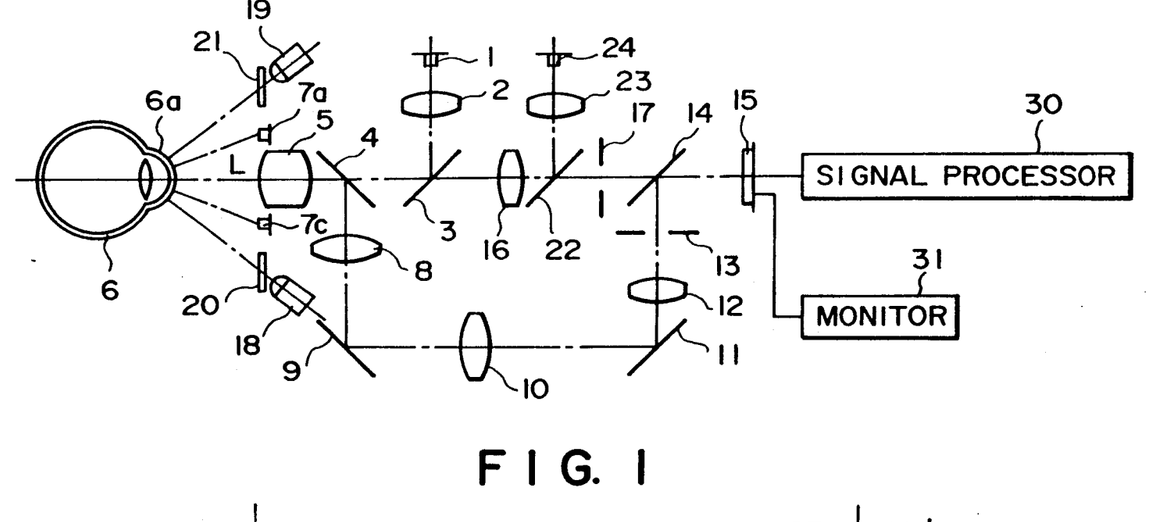
FIG. 1 shows the arrangement of the optical system of a cornea shape measuring apparatus embodying the present invention.

FIG. 1 is an illustration of a first embodiment of the present invention.

Figure 2:
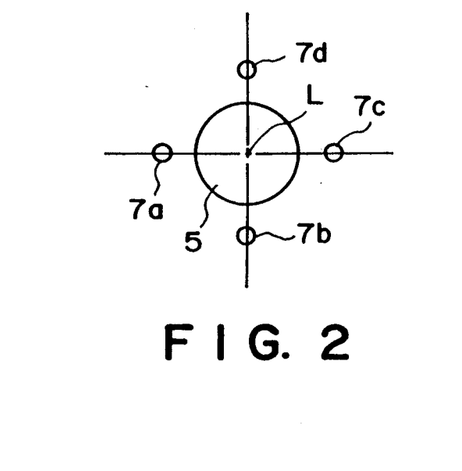
FIG. 2 shows an example of the arrangement of four measuring light sources around the optic axis.

During the measurement of the shape of a cornea, a light emitted from a light source 1 disposed substantially on the optic axis so as to be the center of an ellipse is reflected by a half-mirror 3 through a relay lines 2, is transmitted through a dichroic mirror 4 (which transmits therethrough a light for measuring the shape of the cornea and reflects a light for illuminating the front eye part) and an objective lens 5, and is reflected by the cornea 6a of an eye 6 to be examined. Also, lights emitted from four light sources 7a–7d disposed on the same circumference of a circle about the optic axis L and in the directions of two meridians orthogonal to each other, as shown in FIG. 2, are reflected by the cornea 6a of the eye 6 to be examined.

The reflected images of these light sources 1 and 7a–7d by the cornea 6a of the eye 6 to be examined pass through the objective lens 5, the dichroic mirror 4, the half-mirror 3, a relay lens 16, a half-mirror 22, a stop 17 and a dichroic mirror 14 and are imaged on a two-dimensional image pickup element 15. The stop 17, as known from Japanese Laid-Open Patent Application No. 61-249432, is provided at such a location that the sizes of the cornea-reflected images of the light sources 7a–7d and 1 will not change even if the distance between the apparatus and the eye 6 to be examined changes.

Figure 3:
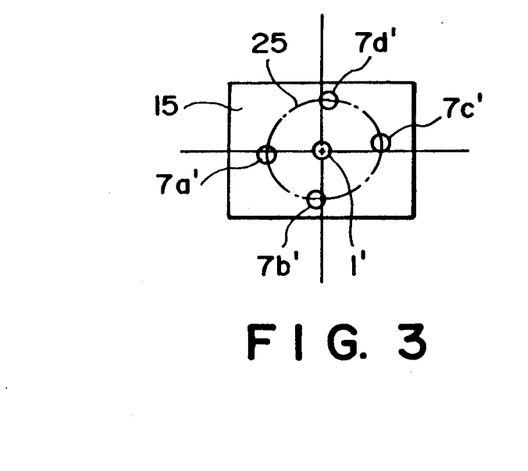
FIG. 3 shows the reflected images, on a two-dimensional image pickup element, of the four measuring light sources around the optic axis and a measuring light source provided on the optic axis reflected by the cornea of an eye to be examined.

FIG. 3 shows the states of the cornea-reflected images of the light sources 7a–7d and 1 projected onto the two-dimensional image pickup element 15, and the reflected images 1' and 7a'–7d' correspond to the light sources 1 and 7a–7d, respectively.

The light source 1 is disposed so as to emit a light always from on the optic axis and therefore, if the light sources 7a–7d are disposed symmetrically about the optic axis, the reflected image 1' will be considered to be the geometrical center relative to the reflected images 7a'-7d' of FIG. 3.

Generally, the cornea is regarded as a toric surface and thus, the cornea-reflected images for such an examinee are such that 7a'-7d' are disposed on an ellipse 25 centered at 1'. On the other hand, the ellipse can be determined if three points are found relative to the center thereof and therefore, can be determined by a signal processor 30 connected to the two-dimensional image pickup element 15 if the coordinates of three of the points 7a'-7d' with 1' as the origin are found. From the thus calculated and determined ellipse, the shape of the cornea of the eye 6 to be examined, i.e., the radii of curvature in the two strong and weak main meridian directions and the axis angle, can be determined. Here, in the signal processor 30, the shape of the cornea found, for example, by the set of 7a', 7b' and 7c' is compared with the shape of the cornea found by the set of 7a', 7b' and 7d' and if the difference therebetween is not so great, the average value thereof is displayed, and if the difference is great, it is displayed that the shape of the cornea is very far from a toric surface and the cornea is of bad astigmatism, whereby the examiner can be informed of that fact. Also, even when one of 7a'-7d' cannot be detected with the examinee's eye partly covered with the eyelid, measurement can be accomplished. That is, when 7d' cannot be detected, an ordinary ellipse passing through 7a', 7b' and 7c' with 1' as the center can be found, whereby the measurement of the shape of the cornea becomes possible.

Now, the light sources 7a-7d need not always be provided on the circumference of the same circle, but the spacing between the light sources 7a and 7c and the spacing between the light sources 7b and 7d may be of different values and the positions of the reflected images on a spherical surface of known curvature for calibration may be stored in advance, and the shape of the cornea can be specified with the positions taken into account.

Now, in FIG. 1, besides the measuring system for the shape of the cornea as described above, a front eye part observation optical system in which the light is reflected by the dichroic mirror 4, is reflected by a mirror 9 through a relay lens 8, is reflected by a mirror 11 through a relay lens 10, is reflected by a dichroic mirror 14 through a stop 13 and passes to the two-dimensional image pickup element 15 and is provided for the observation of the front eye part of the eye 6 to be examined. There are further provided an illuminating optical system comprising lamps 18 and 19 and infrared filters 20 and 21 for the illumination of the front eye part of the eye 6 to be examined, and a fixation optical system comprising a fixation light source 24 for fixating the eye to be examined during measurement, a lens 23 and a dichroic mirror 22. For the purpose of the alignment of the eye 6 to be examined with the apparatus, the measuring light sources 7a-7d are used also as light sources for alignment, and the state in which the cornea-reflected images of the measuring light sources 7a-7d have become clearest on a monitor 31 is judged as the best adjustment of the working distance.

With regard to alignment, the presence of more or less misalignment will not affect the above measurement because provision is made of the measuring light source 1, but adjustment is made so that the cornea-reflected images of the measuring light sources 7a-7d may be positioned within the display field of the monitor 31. In order to facilitate alignment adjustment, for example, a ring-shaped alignment mark may preferably be displayed on the monitor 31.

In this embodiment, in order to avoid the dizziness of the eye to be examined during measurement, the light sources 7a-7d used for measurement and alignment of the eye to be examined and the light source 1 used for measurement are infrared light sources and lights emitted from lamps 18 and 19 used for illuminating the front eye part and passing through filters 20 and 21 are infrared light greatly differing in wavelength from the infrared light sources 7a-7d.

In FIG. 1, the light source 24 for the fixation of the eye to be examined is disposed discretely from the measuring light source 1, but it is also possible to use the measuring light source also as the light source for fixation.

Also, in the above-described first embodiment, the measuring light sources 7a-7d are used also as light sources for alignment, but in FIG. 1, the measuring light source 1 may be used also as a light source for alignment and the light sources 7a-7d may be used exclusively for measurement.

Figure 4A:
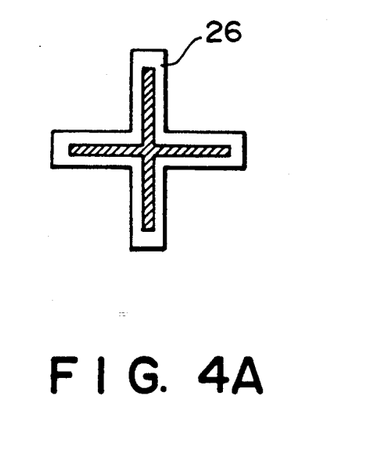
FIGS. 4A and 4B are a plan view and a side view, respectively, when two one-dimensional CCD's intersecting each other are disposed instead of a two-dimensional image pickup element.
Figure 4B:
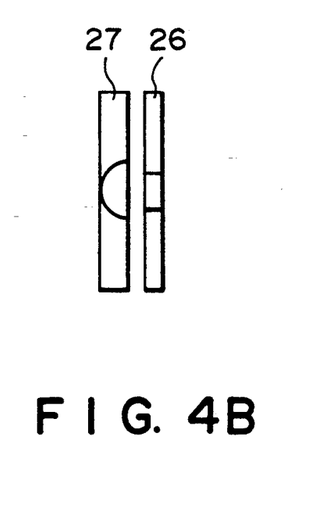

Further, in the above-described first embodiment, the two-dimensional image pickup element is used as a detecting element, whereby it is used also as an image pickup element for the observation of the front eye part, but alternatively, so as to enable the cornea-reflected images to be detected, use may be made of a plurality of one-dimensional CCD's and a condensing lens, for example, one-dimensional CCD's 26 intersecting each other and a cylindrical lens 27 disposed immediately forwardly thereof as shown in FIGS. 4A and 4B, and an image pickup element for the observation of the front eye part may be used independently thereof.

Also, if a ring-shaped light source is provided instead of the four light sources in the first embodiment and from the reflected image thereof, information corresponding to the images of the four light sources, for example, the coordinates of a point at which two particular scanning lines cut the reflected image of the ring, are adopted instead of the images of the four light sources, and the above-described effect can be achieved.

Figure 5:
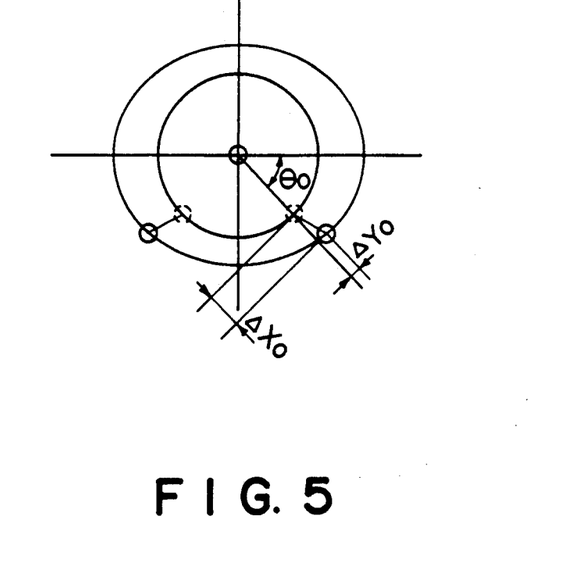
FIG. 5 shows the displacement of the cornea-reflected images of two measuring light sources around the optic axis.

With the reflected image position a when a spherical surface of predetermined curvature is supposed as the reference position, the displacement of the actual reflected image position from the reference position is regarded as a vector and is decomposed into a component with respect to a certain direction $\theta o$ as shown in FIG. 5 to thereby find a component $\Delta x_o$ in the direction $\theta o$ and a component $\Delta y_o$ in a direction perpendicular to the direction $\theta o$, whereby the four light sources on the circumference of the same circle in the first embodiment may be two and thereby, an ellipse can be specified and the shape of the cornea can be measured.

Figure 6:
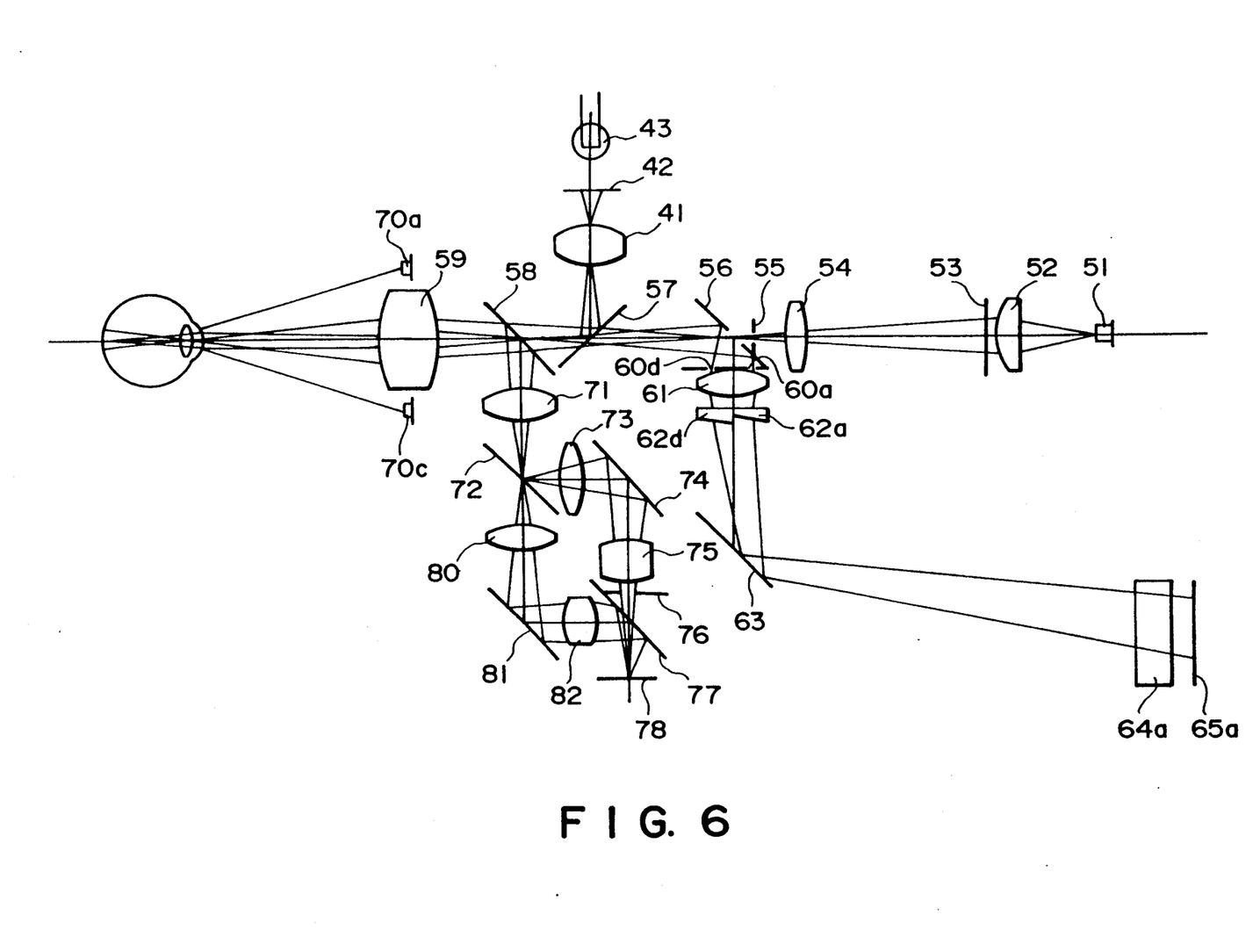
FIG. 6 shows an embodiment in which the measurement of the shape of a cornea is effected with an index mark for measuring eye refractive power being used also as an index mark for measuring the shape of the cornea.

FIG. 6 shows an embodiment in which the index mark for measuring the eye refractive power is used also as the index mark for measuring the shape of the cornea to thereby effect the measurement of the shape of the cornea. The measurement of the eye refractive power is such that a light emitted from a light source 51 illuminates an index mark 53 for measuring the eye refractive power through a condensing lens 52 and the index mark 53 for measuring the eye refractive power is transmitted through a stop 55 and an aperture in an apertured mirror 56 by means of a relay lens 54 and is further transmitted through light-dividing mirrors 57 and 58 and is projected onto the fundus of the eye to be examined through an objective lens 59. Also, the reflected image of the index mark 53 for measuring the eye refractive power by the fundus of the eye is transmitted through the light-dividing mirrors 58 and 57 and through the objective lens 59, is reflected by the apertured mirror 56, is transmitted through openings 60a-60f in a multi-apertured aperture stop 60, is separated and deflected by a relay lens 61 and prisms 62a-62f, is reflected by a mirror 63, and is imaged on one-dimensional position detecting elements 65a-65c such as one-dimensional CCD's through cylindrical lenses 64a-64c. The cylindrical lenses 64a-64c each have power in a direction perpendicular to the direction of detection of the one-dimensional position detecting elements 65a-65c, and condense the light in that direction on the corresponding one-dimensional position detecting elements.

Figure 7:
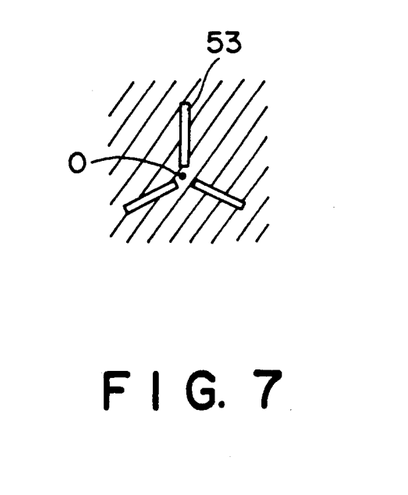
FIG. 7 shows a specific example of the index mark for measuring the eye refractive power.
Figure 8:
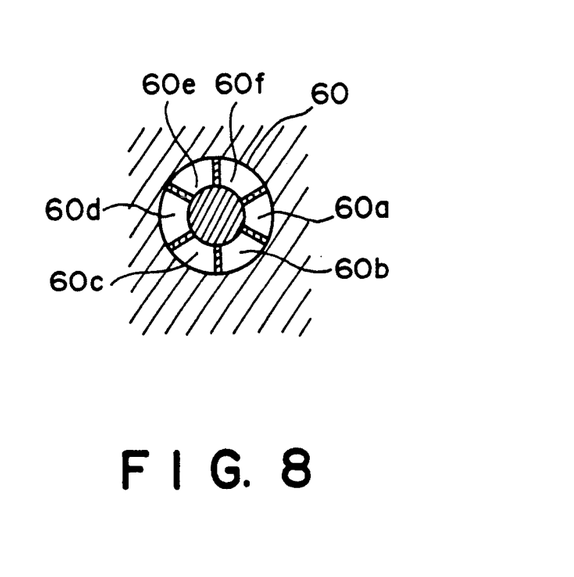
FIG. 8 is an enlarged view of a stop.
Figure 9:
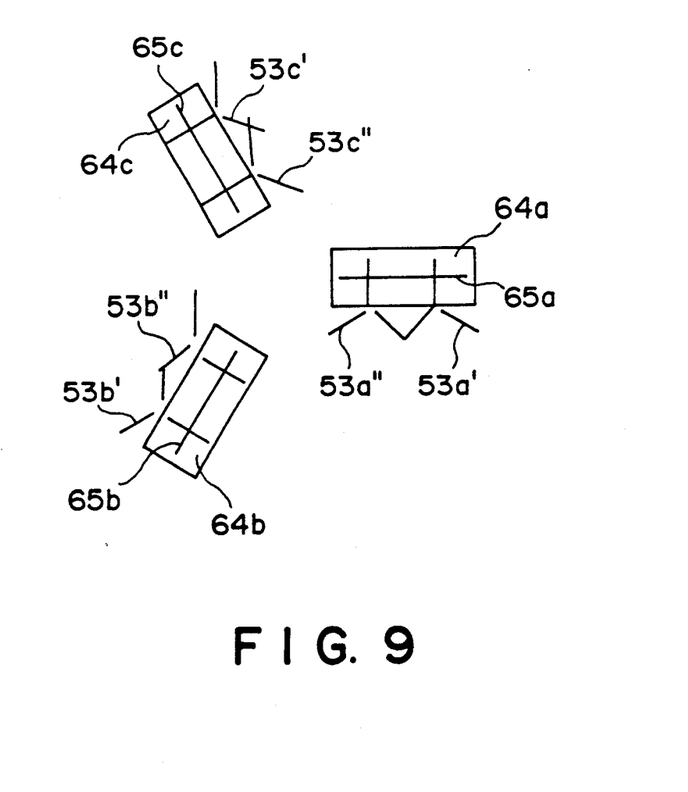
FIG. 9 shows the reflected image by the fundus of an eye on an image position detecting element.

The index mark 53 for measuring the eye refractive power is of such a shape as shown in FIG. 7, and the center O thereof is disposed on the optic axis. The reflected image of the index mark 53 for measuring the eye refractive power by the fundus of the eye is separated into six images through openings 60a-60f in a multi-apertured stop 60 (substantially conjugate with the pupil of the eye to be examined) shown in FIG. 8. If the fundus of the eye to be examined is conjugate with the position detecting elements 65, the originally six separated images will be superposed on the optic axis, but they remain six separated images by the presence of the prisms 62a-62f. So, the eye refractive power is found on the basis of the spacing between 53a' and 53a'' appearing in the signals of the one-dimensional position detecting elements 65a-65c.

Figure 10:
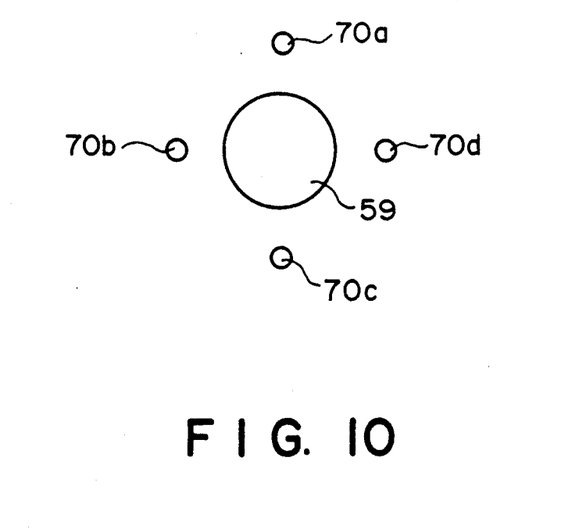
FIG. 10 shows a specific example of the index mark for measuring the shape of the cornea.
Figure 11:
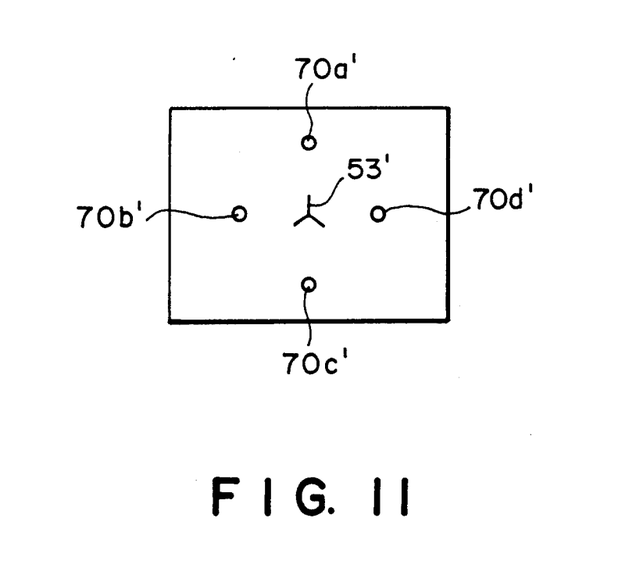
FIG. 11 shows the cornea-reflected images on image pickup means.

On the other hand, for the measurement of the shape of the cornea, use is made of four index marks 70a-70d arranged as shown in FIG. 10 and the index mark 53 for measuring the eye refractive power. Lights which have left the index marks 70a-70d are reflected by the cornea, are reflected by the light-dividing mirror 58 through the objective lens 59, are once imaged by a relay lens 71, are reflected by a light-dividing mirror 72, are transmitted through a field lens 73, are reflected by a mirror 74, are transmitted through a relay lens 75 and through a stop 76 and a light-combining mirror 77, and are again imaged on a two-dimensional image pickup element 78. The stop 76 is similar to the stop 17 of FIG. 1, and is disposed at such a position that the magnifications of the index marks 70a-70d are invariable even if the working distance between the apparatus and the eye to be examined varies, i.e., a position at which the principal light ray connecting the cornea-reflected images (virtual images) of the index marks 70 (70a-70d) in the eye to be examined when the working distance is proper and when the working distance is improper intersects the optic axis through the above-described optical system. Here, the cornea-reflected image of the index mark 53 for measuring the eye refractive power is also imaged on the image pickup element 78 through the above-described optical system, and FIG. 11 shows the states of the cornea-reflected images of the index marks 70a-70d and the index mark 53 for measuring the eye refractive power on the image pickup element 78. The respective reflected images are represented with ' suffixed thereto.

Now, the index mark 53 for measuring the eye refractive power always emerges from on the optic axis and therefore, if the index marks 70a-70d for measuring the shape of the cornea are disposed symmetrically about the optic axis, the cornea-reflected image 53' is considered to be the geometrical center of the cornea-reflected images 70a'-70d'. Generally the cornea is a toric surface and thus, the cornea-reflected images relative to such an examinee are such that the images 70a'-70d' are disposed on a certain ellipse centered at the image 53'.

On the other hand, the ellipse can be determined if three points are determined relative to a certain center and therefore, the ellipse can be determined if the positional coordinates of three of the images 70a'-70d' having the center of the image 53' as the origin are found.

Here, if the center of the image 53' is defined as the origin and the distances from this origin to the images 70a'-70d' are compared with one another, the presence of bad astigmatism can be detected. If when determining the ellipse, the ellipse determined, for example, by the set of images 70a', 70b' and 70c' and the ellipse determined by the set of images 70b', 70c' and 70d' are compared with each other and their shapes do not differ greatly from each other, the average value thereof may be displayed, and if their shapes differ greatly from each other, they may be judged to be not a toric surface and a bad astigmatism mark indicative of an abnormal shape may be displayed, thereby informing the examiner. It is apparent that even when the eye to be examined is partly covered with the eyelid and the image 70a' cannot be detected, it is possible to display the measured value by the use of the images 70b', 70c' and 70d'. Also, a similar effect may be obtained if as a modification, the positions of the images 70a'-70d' are calibrated in advance by a spherical surface or the like having a known curvature even though the index marks 70a-70d are not disposed symmetrically about the optic axis.

Now, in FIG. 6, there is shown, in addition to the aforedescribed two measuring systems, a front eye part observation optical system which is separated from the cornea shape measuring optical system by the light-dividing mirror 72, a field lens 80, a mirror 81 and a relay lens 82 and is again combined with the cornea shape measuring optical system by the light-combining mirror 77. Further shown is a fixation target optical system for making the examinee fixate his eyes during the cornea shape measurement and the eye refractive power measurement, and specifically, this is comprised of an illuminating optical system 43, a fixation target 42 movable in the direction of the optic axis, a relay lens 41, the light-dividing mirrors 57, 58 and the objective lens 59.

In FIG. 6, the index mark 53 for measuring the eye refractive power is shown with its center lying on the optic axis, but even if apparently the center is off the optic axis, there will be no problem if the index marks 70a-70d are calibrated in advance by a spherical surface or the like having a known curvature, as previously described.

This is because even in this case, in the present invention, the center of the index mark for measuring the eye refractive power is considered to be substantially on the optic axis.

While in the embodiment of FIG. 6, three one-dimensional position detecting elements are used for the measurement of the eye refractive power, these elements may be replaced by two-dimensional image pickup elements or further, a bypass optical path may be utilized so that the image pickup element 78 may be used also as these elements. Also, design may be made such that the optical system is moved to thereby find the position conjugate with the fundus of the eye from the balance of the quantity of light.

The index mark 53 for measuring the eye refractive power and the index marks 70 (70a–70d) for measuring the shape of the cornea are not restricted to those described above, but may be, for example, of a ring shape.

We claim:

1. An ophthalmic apparatus capable of measuring the shape of a cornea, comprising:
    an index mark adapted to be projected onto the cornea of an eye to be examined, said index mark being provided with a first index mark positioned substantially on an optic axis and a second index mark positioned around the optic axis;
    an imaging optical system for re-imaging the cornea-reflected images of said first and second index marks;
    light position detecting means provided at the image plane position of said imaging optical system for detecting the position of the cornea-reflected images of said first and second image marks; and
    calculating means for calculating the information of the shape of the cornea based on the position information of the cornea-reflected image of both said first index mark and said second index mark detected by said light position detecting means.

2. An ophthalmic apparatus according to claim 1, wherein said first index mark is a light source which comprises an alignment light source.

3. An ophthalmic apparatus according to claim 1, wherein said first index mark is a light source comprising a fixation light source.

4. An ophthalmic apparatus according to claim 1, wherein said second index mark is a ring-shaped light source.

5. An ophthalmic apparatus according to claim 1, wherein said first and second index marks are infrared light sources.

6. An ophthalmic apparatus according to claim 1, wherein said light position detecting means is a two-dimensional image pickup element.

7. An ophthalmic apparatus according to claim 1, wherein said light position detecting means is a plurality of one-dimensional charged coupled devices.

8. An ophthalmic apparatus capable of measuring the shape of a cornea, comprising:
    an index mark adapted to be projected onto the cornea of an eye to be examined, said index mark being provided with a first index mark positioned substantially on an optic axis and a second index mark positioned around the optic axis;
    an imaging optical system for re-imaging the cornea-reflected images of said first and second index marks;
    light position detecting means provided at the image plane position of said imaging optical system for detecting the position of the cornea-reflected images of said first and second image marks; and
    calculating means for calculating the information of the shape of the cornea based on the position information of the cornea-reflected image of both said first index mark and said second index mark detected by said light position detecting means,
    wherein said second index mark includes at least three points on the circumference of the same circle.

9. An ophthalmic apparatus according to claim 8, wherein said second index mark includes four point sources of light provided in two meridian directions orthogonal to each other.

10. An ophthalmic apparatus capable of measuring the shape of a cornea, comprising:
    an index mark adapted to be projected onto the cornea of an eye to be examined, said index mark being provided with a first index mark positioned substantially on an optic axis and a second index mark positioned around the optic axis;
    an imaging optical system for re-imaging the cornea-reflected images of said first and second index marks;
    light position detecting means provided at the image plane position of said imaging optical system for detecting the position of the cornea-reflected images of said first and second image marks; and
    calculating means for calculating the information of the shape of the cornea based on the position information of the cornea-reflected image of both said first index mark and said second index mark detected by said light position detecting means,
    wherein said second index mark includes at least three points which are not on the circumference of the same circle, and said calculating means stores in advance the position of the reflected image on a spherical surface for calibration.

11. An ophthalmic apparatus capable of measuring the shape of a cornea, comprising:
    an index mark adapted to be projected onto the cornea of an eye to be examined, said index mark being provided with a first index mark positioned substantially on an optic axis and a second index mark positioned around the optic axis;
    an imaging optical system for re-imaging the cornea-reflected images of said first and second index marks;
    light position detecting means provided at the image plane position of said imaging optical system for detecting the position of the cornea-reflected images of said first and second image marks; and
    calculating means for calculating the information of the shape of the cornea based on the position information of the cornea-reflected image of both said first index mark and said second index mark detected by said light position detecting means,
    wherein said second index mark includes at least two points, and said calculating means calculates the deflection vector of the cornea-reflected image of said second index mark with the position information of the reflected image of said second index mark on a predetermined spherical surface as the reference.

12. An ophthalmic apparatus comprising:
    a first index mark, attached to said apparatus, positioned substantially on an optic axis and adapted to be projected onto the fundus of an eye to be examined;
    a second index mark, attached to said apparatus, positioned around the optic axis and adapted to be projected onto the cornea of the eye to be examined;
    first measuring means, attached to said apparatus, for receiving the eye-fundus-reflected image light of said first index mark and for measuring the eye refractive power of the eye to be examined; and
    second measuring means, attached to said apparatus, for receiving the cornea-reflected image lights of both said first and second index marks and for measuring the shape of the cornea of the eye to be examined.

13. An ophthalmic apparatus according to claim 12, wherein said second index mark is a ring-shaped light source.

14. An ophthalmic apparatus according to claim 12, wherein said first and second index marks are infrared light sources.

15. An ophthalmic apparatus according to claim 12, wherein said second measuring means has a two-dimensional image pickup element.

16. An ophthalmic apparatus according to claim 12, wherein said second measuring means has a plurality of one-dimensional charged coupled devices.

17. An ophthalmic apparatus comprising:
a first index mark, attached to said apparatus, positioned substantially on an optic axis and adapted to be projected onto the fundus of an eye to be examined;
a second index mark, attached to said apparatus, positioned around the optic axis and adapted to be projected onto the cornea of the eye to be examined;
first measuring means, attached to said apparatus, for receiving the eye-fundus-reflected image light of said first index mark and for measuring the eye refractive power of the eye to be examined; and
second measuring means, attached to said apparatus, for receiving the cornea-reflected image lights of both said first and second index marks and for measuring the shape of the cornea of the eye to be examined,
wherein said second index mark includes at least three points on the circumference of the same circle.

18. An ophthalmic apparatus according to claim 17, wherein said second index mark includes four point sources of light provided in two meridian directions orthogonal to each other.

19. An ophthalmic apparatus comprising:
a first index mark, attached to said apparatus, positioned substantially on an optic axis and adapted to be projected onto the fundus of an eye to be examined;
a second index mark, attached to said apparatus, positioned around the optic axis and adapted to be projected onto the cornea of the eye to be examined;
first measuring means, attached to said apparatus, for receiving the eye-fundus-reflected image light of said first index mark and for measuring the eye refractive power of the eye to be examined; and
second measuring means, attached to said apparatus, for receiving the cornea-reflected image lights of both said first and second index marks and for measuring the shape of the cornea of the eye to be examined,
wherein said second index mark includes at least three points which are not on the circumference of the same circle, and said second measuring means stores in advance the position of the reflected image on a spherical surface for calibration.

20. An ophthalmic apparatus comprising:
a first index mark, attached to said apparatus, positioned substantially on an optic axis and adapted to be projected onto the fundus of an eye to be examined;
a second index mark, attached to said apparatus, positioned around the optic axis and adapted to be projected onto the cornea of the eye to be examined;
first measuring means, attached to said apparatus, for receiving the eye-fundus-reflected image light of said first index mark and for measuring the eye refractive power of the eye to be examined; and
second measuring means, attached to said apparatus, for receiving the cornea-reflected image lights of both said first and second index marks and for measuring the shape of the cornea of the eye to be examined,
wherein said second index mark includes at least two points, and said second measuring means determines the deflection vector of the cornea-reflected image of said second index mark with the position information of the reflected image of said second index mark on a predetermined spherical surface as the reference.

21. An ophthalmic apparatus capable of measuring the shape of a cornea, comprising:
an index mark adapted to be projected onto the cornea of an eye to be examined, said index mark being provided with a first index mark and a second index mark, said second index mark being positioned around an optic axis;
an imaging optical system for re-imaging cornea-reflected images of said first and second index marks;
light position detecting means provided at the image plane position of said imaging optical system for detecting the position of the cornea-reflected images of said first and second index marks, wherein said cornea-reflected image of said first index mark indicates information of the position of the optic axis relative to the cornea on said light position detecting means; and
calculating means for calculating information of the shape of the cornea based on the position information of the cornea-reflected image of both said first index mark and said second index mark detected by said light position detecting means.

22. An ophthalmic apparatus according to claim 21, wherein said first index mark is a light source which comprises an alignment light source.

23. An ophthalmic apparatus according to claim 21, wherein said first index mark is a light source comprising a fixation light source.

24. An ophthalmic apparatus according to claim 21, wherein said second index mark is a ring-shaped light source.

25. An ophthalmic apparatus according to claim 21, wherein said first and second index marks are infrared light sources.

26. An ophthalmic apparatus according to claim 21, wherein said light position detecting means is a two-dimensional image pickup element.

27. An ophthalmic apparatus according to claim 21, wherein said light position detecting means is a plurality of one-dimensional charged coupled devices.

28. An ophthalmic apparatus capable of measuring the shape of a cornea, comprising:
an index mark adapted to be projected onto the cornea of an eye to be examined, said index mark being provided with a first index mark and a second index mark, said second index mark being positioned around an optic axis;

an imaging optical system for re-imaging cornea-reflected images of said first and second index marks;

light position detecting means provided at the image plane position of said imaging optical system for detecting the position of the cornea-reflected images of said first and second index marks, wherein said cornea-reflected image of said first index mark indicates information of the position of the optic axis relative to the cornea on said light position detecting means; and calculating means for calculating information of the shape of the cornea based on the position information of the cornea-reflected image of both said first index mark and said second index mark detected by said light position detecting means, wherein said second index mark includes at least three points on the circumference of the same circle.

29. An ophthalmic apparatus according to claim 28, wherein said second index mark includes four point sources of light provided in two meridian directions orthogonal to each other.

30. An ophthalmic apparatus capable of measuring the shape of a cornea, comprising:

an index mark adapted to be projected onto the cornea of an eye to be examined, said index mark being provided with a first index mark and a second index mark, said second index mark being positioned around an optic axis;

an imaging optical system for re-imaging cornea-reflected images of said first and second index marks;

light position detecting means provided at the image plane position of said imaging optical system for detecting the position of the cornea-reflected images of said first and second index marks, wherein said cornea-reflected image of said first index mark indicates information of the position of the optic axis relative to the cornea on said light position detecting means; and calculating means for calculating information of the shape of the cornea based on the position information of the cornea-reflected image of both said first index mark and said second index mark detected by said light position detecting means, wherein said second index mark includes at least three points which are not on the circumference of the same circle, and said calculating means stores in advance the position of the reflected image on a spherical surface for calibration.

31. An ophthalmic apparatus capable of measuring the shape of a cornea, comprising:

an index mark adapted to be projected onto the cornea of an eye to be examined, said index mark being provided with a first index mark and a second index mark, said second index mark being positioned around an optic axis;

an imaging optical system for re-imaging cornea-reflected images of said first and second index marks;

light position detecting means provided at the image plane position of said imaging optical system for detecting the position of the cornea-reflected images of said first and second index marks, wherein said cornea-reflected image of said first index mark indicates information of the position of the optic axis relative to the cornea on said light position detecting means; and calculating means for calculating information of the shape of the cornea based on the position information of the cornea-reflected image of both said first index mark and said second index mark detected by said light position detecting means, wherein said second index mark includes at least two points, and said calculating means calculates the deflection vector of the cornea-reflected image of said second index mark with the position information of the reflected image of said second index mark on a predetermined spherical surface as the reference.

32. An ophthalmic apparatus comprising:

a first index mark, attached to said apparatus, adapted to be projected onto the fundus of an eye to be examined, said first index mark being positioned so that a cornea-reflected image of said first index mark indicates information of the position of an optic axis relative to the cornea;

a second index mark, attached to said apparatus, positioned around the optic axis and adapted to be projected onto the cornea of the eye to be examined;

first measuring means, attached to said apparatus, for receiving an eye-fundus-reflected image light of said first index mark and for measuring the eye refractive power of the eye to be examined; and second measuring means, attached to said apparatus, for receiving cornea-reflected image lights of both said first and second index marks and for measuring the shape of the cornea of the eye to be examined.

33. An ophthalmic apparatus according to claim 32, wherein said second index mark is a ring-shaped light source.

34. An ophthalmic apparatus according to claim 32, wherein said first and second index marks are infrared light sources.

35. An ophthalmic apparatus according to claim 32, wherein said second measuring means has a two-dimensional image pickup element.

36. An ophthalmic apparatus according to claim 32, wherein said second measuring means has a plurality of one-dimensional charged coupled devices.

37. An ophthalmic apparatus, comprising:

a first index mark, attached to said apparatus, adapted to be projected onto the fundus of an eye to be examined, said first index mark being positioned so that a cornea-reflected image of said first index mark indicates information of the position of an optic axis relative to the cornea;

a second index mark, attached to said apparatus, positioned around the optic axis and adapted to be projected onto the cornea of the eye to be examined;

first measuring means, attached to said apparatus, for receiving the eye-fundus-reflected image light of said first index mark and for measuring the eye refractive power of the eye to be examined; and second measuring means, attached to said apparatus, for receiving the cornea-reflected image lights of both said first and second index marks and for measuring the shape of the cornea of the eye to be examined, wherein said second index mark includes at least three points on the circumference of the same circle.

38. An ophthalmic apparatus according to claim 37, wherein said second index mark includes four point sources of light provided in two meridian directions orthogonal to each other.

39. An ophthalmic apparatus, comprising:
- a first index mark, attached to said apparatus, adapted to be projected onto the fundus of an eye to be examined, said first index mark being positioned so that a cornea-reflected image of said first index mark indicates information of the position of an optic axis relative to the cornea;
- a second index mark, attached to said apparatus, positioned around the optic axis and adapted to be projected onto the cornea of the eye to be examined;
- first measuring means, attached to said apparatus, for receiving the eye-fundus-reflected image light of said first index mark and for measuring the eye refractive power of the eye to be examined; and
- second measuring means, attached to said apparatus, for receiving the cornea-reflected image lights of both said first and second index marks and for measuring the shape of the cornea of the eye to be examined,
- wherein said second index mark includes at least three points which are not on the circumference of the same circle, and said second measuring means stores in advance the position of the reflected image on a spherical surface for calibration.

40. An ophthalmic apparatus, comprising:
- a first index mark, attached to said apparatus, adapted to be projected onto the fundus of an eye to be examined, said first index mark being positioned so that a cornea-reflected image of said first index mark indicates information of the position of an optic axis relative to the cornea;
- a second index mark, attached to said apparatus, positioned around the optic axis and adapted to be projected onto the cornea of the eye to be examined;
- first measuring means, attached to said apparatus, for receiving the eye-fundus-reflected image light of said first index mark and for measuring the eye refractive power of the eye to be examined; and
- second measuring means, attached to said apparatus, for receiving the cornea-reflected image lights of both said first and second index marks and for measuring the shape of the cornea of the eye to be examined,
- wherein said second index mark includes at least two points, and said second measuring means determines the deflection vector of the cornea-reflected image of said second index mark with the position information of the reflected image of said second index mark on a predetermined spherical surface as the reference.

* * * * *

UNITED STATES PATENT AND TRADEMARK OFFICE
CERTIFICATE OF CORRECTION

PATENT NO. : 5,302,979
DATED : April 12, 1994
INVENTOR(S) : YASUO MAEDA, ET AL.

It is certified that error appears in the above-indentified patent and that said Letters Patent is hereby corrected as shown below:

COLUMN 1

Line 17, "ring-shape" should read -- ring-shaped --.
Line 26, "the shape" should read -- the shape of which --, and "shape of" should read -- shape, --.
Line 27, "which" should be deleted.
Line 38, "ring-shape" should read -- ring-shaped --.
Line 45, "fins" should read -- finds --.

COLUMN 2

Line 37, "lines 2," should read -- lens 2, --.

COLUMN 4

Line 44, delete "a" (first occurrence).

COLUMN 7

Line 44, "charged" should read -- charge --.

COLUMN 9

Line 14, "charged" should read -- charge --.

UNITED STATES PATENT AND TRADEMARK OFFICE
CERTIFICATE OF CORRECTION

PATENT NO. : 5,302,979

DATED : April 12, 1994

INVENTOR(S) : YASUO MAEDA, ET AL.

It is certified that error appears in the above-indentified patent and that said Letters Patent is hereby corrected as shown below:

COLUMN 10

Line 61, "charged" should read -- charge --.

COLUMN 12

Line 45, "charged" should read -- charge --.

Signed and Sealed this

Eleventh Day of October, 1994

Attest:

BRUCE LEHMAN

Attesting Officer     Commissioner of Patents and Trademarks